United States Patent [19]
Corvelli et al.

[11] Patent Number: 5,941,884
[45] Date of Patent: Aug. 24, 1999

[54] PATELLA PREPARATION APPARATUS AND METHOD

[75] Inventors: Amy A. Corvelli, Montville; Arthur S. Heissenbuttel, Glen Rock; Yu Chang Lin, Plainsboro; Bryan J. Smith, Summit, all of N.J.

[73] Assignee: Osteonics Corp., Allendale, N.J.

[21] Appl. No.: 09/169,030

[22] Filed: Oct. 9, 1998

[51] Int. Cl.⁶ .................................................. A61B 17/56
[52] U.S. Cl. ............................................ 606/88; 606/102
[58] Field of Search ............................ 606/88, 87, 86, 606/82, 79, 102

[56] References Cited

U.S. PATENT DOCUMENTS

| | | |
|---|---|---|
| 4,633,862 | 1/1987 | Petersen . |
| 4,706,660 | 11/1987 | Petersen . |
| 5,021,055 | 6/1991 | Burkinshaw et al. . |
| 5,129,907 | 7/1992 | Heldreth et al. . |
| 5,129,908 | 7/1992 | Petersen . |
| 5,222,955 | 6/1993 | Mikhail . |
| 5,295,992 | 3/1994 | Cameron . |
| 5,486,177 | 1/1996 | Mumme et al. . |
| 5,520,692 | 5/1996 | Ferrante ........................... 606/88 |
| 5,536,271 | 7/1996 | Daly et al. ........................ 606/80 |
| 5,575,793 | 11/1996 | Carls et al. ...................... 606/80 |
| 5,658,291 | 8/1997 | Techiera ........................... 606/80 |

*Primary Examiner*—Guy V. Tucker
*Attorney, Agent, or Firm*—Arthur Jacob

[57] ABSTRACT

A patella clamp and method for use in resecting a patella for the reception of a patellar prosthesis holds the patella in a preparation position and provides the surgeon with a direct and interoperative accurate visual indication of the bone thickness of the patella prior to and subsequent to resection, as well as a direct and interoperative accurate visual indication of an interoperatively settable depth of resection, all without the necessity for introducing supplemental instruments or other apparatus during the resection procedure.

11 Claims, 7 Drawing Sheets

//www.w3.org/1999/xhtml">
PATELLA PREPARATION APPARATUS AND METHOD

The present invention relates generally to the implant of patellar protheses and pertains, more specifically, to apparatus and method for the preparation of a natural patella for the reception of a patellar prosthesis.

Knee replacement has become an important option available in the treatment of a natural knee joint which has become deteriorated as a result of injury or disease. Replacement of the natural knee with a prosthetic knee joint has become relatively commonplace and a variety of prosthetic knee implant components, and related implant instrument systems and procedures, currently are available. Improvements are being sought continually not only in the design and construction of the implant components themselves, but in instruments and procedures which can facilitate implant through reductions in complexity, with concomitant reductions in operating time and trauma, and increased accuracy.

The present invention provides improved apparatus and method for facilitating the preparation of the natural patella to receive a patellar prosthesis. As such, the present invention attains several objects and advantages, some of which are summarized as follows: Enables increased ease and accuracy in effecting removal of predetermined amounts of natural bone for resection of the posterior patella in preparing the patella for reception of a patellar prosthesis; allows interoperative selection of the depth of resection with increased ease and accuracy, and without the necessity for interchanging component parts of the apparatus; permits immediate and accurate measurement of patella bone thickness prior to resection and then subsequent to resection, interoperatively, without requiring supplemental apparatus or component parts; facilitates the overall procedure for implanting a patellar prosthesis, thereby reducing operating time and concomitant trauma to the patient, while promoting greater precision in effecting the implant; provides a surgeon with greater versatility and a wider range of options during the implant procedure, with instruments of reduced complexity and increased ease of use; makes available apparatus of simplified and rugged construction, capable of reliable use with repeated accuracy over an extended service life.

The above objects and advantages, as well as further objects and advantages, are attained by the present invention which may be described briefly as apparatus for the preparation of a patella to receive a patellar prosthesis on a resected surface located at a selected depth of resection, the patella having an anterior surface, a posterior surface and a bone thickness between the anterior surface and the posterior surface, the preparation including resection of the bone of the patella to the selected depth of resection, the apparatus comprising: a frame; a reference platform on the frame for supporting the patella in a preparation position, the reference platform including a reference platform surface extending laterally along the reference platform such that the anterior surface of the patella is located against the reference platform surface when the patella is in the preparation position; a retaining member for mounting upon the frame in juxtaposition with the reference platform to hold the patella in the preparation position; a bushing member for mounting upon the frame in juxtaposition with the reference platform, the bushing member including a longitudinal axis for intersecting the reference platform at the preparation position; a tool holder for carrying a bone-cutting tool, the tool holder being receivable within the bushing member for linear movement along the longitudinal axis toward and away from the reference platform, and for rotational movement about the longitudinal axis, to locate and move the bone-cutting tool in juxtaposition with the reference platform; a first indicator for direct interoperative indication of the longitudinal distance between the bone-cutting tool and the reference platform surface and, consequently, the bone thickness of the patella when the patella is in the preparation position and the bone-cutting tool is placed against the patella; a first reference surface on the bushing member and extending laterally along the bushing member; a stop member mounted on the tool holder for selective movement longitudinally along the tool holder interoperatively, the stop member having a second reference surface for juxtaposition in opposition to the first reference surface and including a coupler for interoperative coupling of the stop member with the tool holder at a selected location along the longitudinal axis, at which selected location the longitudinal spacing between the first reference surface and the second reference surface determines a desired depth of resection of the bone of the patella; and a second indicator for direct interoperative indication of the selected location of the stop member and, consequently, the selected depth of resection.

In addition, the invention includes a method for the implant of a patellar prosthesis on a resected surface of a natural patella, the patella having an anterior surface, a posterior surface and a bone thickness between the anterior surface and the posterior surface, the method including resection of the bone of the patella to locate the resected surface at a selected depth of resection, the method comprising the steps of: supporting the patella in a preparation position on a reference platform surface extending laterally along a reference platform such that the anterior surface of the patella is located against the reference platform surface when the patella is in the preparation position; holding the patella in the preparation position; juxtaposing a bushing member with the reference platform, the bushing member including a longitudinal axis for intersecting the reference platform at the preparation position; placing a tool holder within the bushing member for carrying a bone-cutting tool for linear movement along the longitudinal axis toward and away from the reference platform, and for rotational movement about the longitudinal axis, to enable location and movement of the bone-cutting tool in juxtaposition with the reference platform; providing a first indicator on the tool holder for direct and interoperative visual indication of the longitudinal distance between the bone-cutting tool and the reference platform surface and, consequently, the bone thickness of the patella when the patella is in the preparation position; placing the bone-cutting tool against the posterior surface of the patella held in the preparation position to determine the bone thickness of the patella directly and interoperatively, prior to resection; providing a first reference surface on the bushing member and extending laterally along the bushing member; selectively moving a stop member longitudinally along the tool holder interoperatively, the stop member having a second reference surface for juxtaposition in opposition to the first reference surface, and interoperatively coupling the stop member with the tool holder at a selected location along the longitudinal axis, at which selected location the longitudinal spacing between the first reference surface and the second reference surface determines a desired depth of resection of the bone of the patella; providing a second indicator on the bushing member for direct and interoperative visual indication of the selected location of the stop member and, consequently, direct determination of the selected depth of resection; advancing the bone-cutting tool longitudinally along the longitudinal axis until the second reference surface engages the first reference surface; and viewing the first indicator for a direct and interoperative indication of the bone thickness of the patella subsequent to resection.

The present invention will be understood more fully, while still further objects and advantages will become apparent in the following detailed description of preferred embodiments of the invention illustrated in the accompanying drawing, in which.

Figure 1:
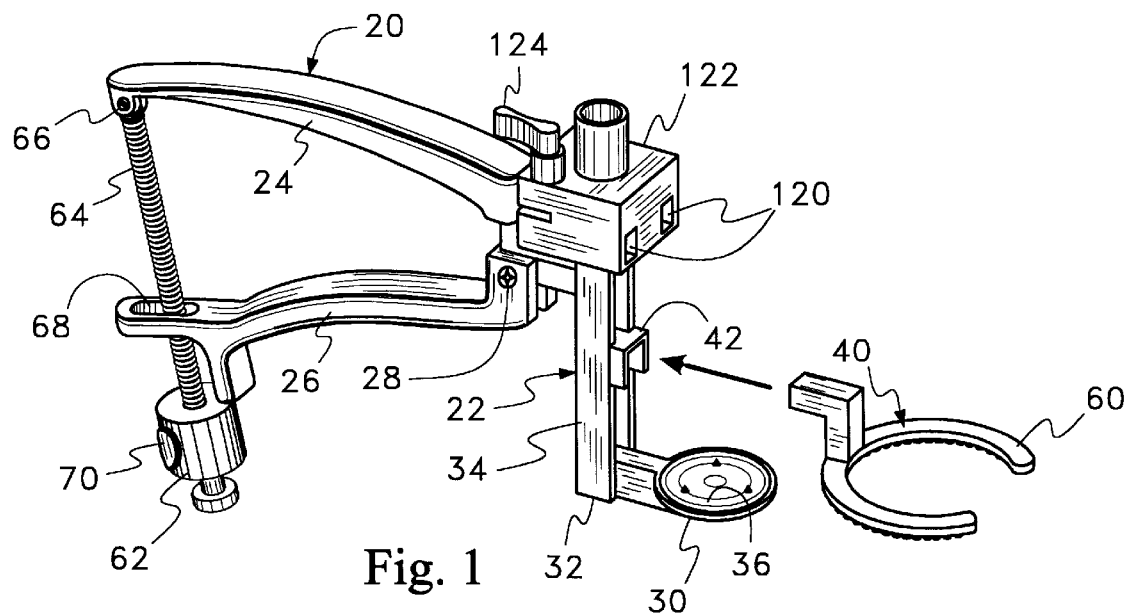
FIG. 1 is a pictorial perspective view, partially exploded, of a portion of an apparatus constructed in accordance with the present invention.

Referring now to the drawing, and especially to FIG. 1 thereof, an apparatus constructed in accordance with the present invention is shown in the form of a patella clamp 20 having a frame 22. An upper handle 24 is affixed to the frame 22 and a lower handle 26 is mounted upon the frame 22 at 28 for pivotal movement toward and away from the upper handle 24. A reference platform 30 is integral with the frame 22 at lower end 32 of a clamp bar 34 of the frame 22 and includes a reference platform surface 36 extending laterally across the reference platform 30. A retaining member shown in the form of a tendon clamp member 40 is to be received within a carrier 42 mounted for movement along the clamp bar 34 and coupled with the lower handle 26 so that pivotal movement of the lower handle 26 will move the carrier 42 longitudinally along the clamp bar 34 toward and away from the reference platform 30.

Figure 2:
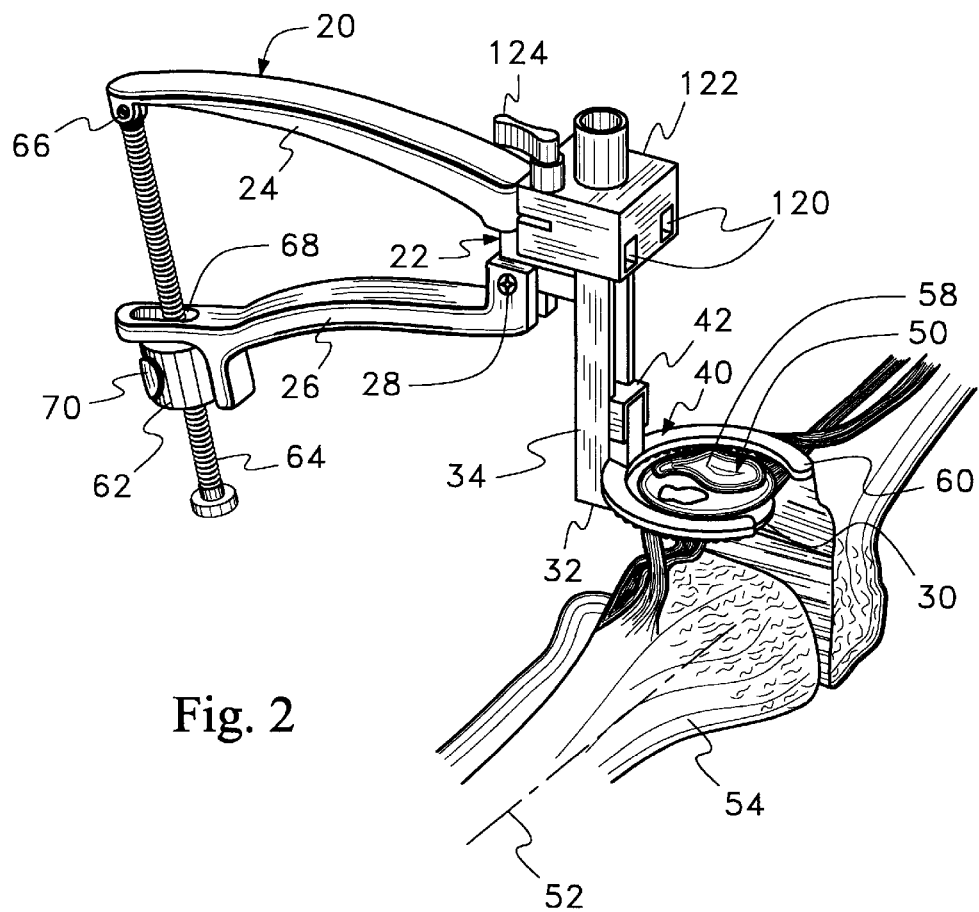
FIG. 2 is a pictorial perspective view of the portion of the apparatus applied to an everted patella.

As best seen in FIG. 2, with the tendon clamp member 40 in place within the carrier 42, a patella 50 which is to be prepared for the reception of a patellar prosthesis, is held in a preparation position within the patella clamp 20 by everting the patella 50 and applying the patella clamp 20 to the everted patella 50, with the handles 24 and 26 essentially perpendicular to the long axis 52 of the leg 54 of the patient, as shown. The patella 50 includes an anterior surface 56, which is located on the reference platform surface 36 of the reference platform 30 (see FIG. 6), and a posterior surface 58, the patella 50 having a bone thickness extending between the anterior surface 56 and the posterior surface 58. The posterior surface 58 provides the articular surface of the patella 50 and is to be prepared for the reception of a patellar prosthesis. In the preferred construction, reference platform surface 36 of the reference platform 30 is concave so as to provide a somewhat cupped configuration for facilitating accommodation of the convex anterior surface 56 of the patella 50.

The tendon clamp member 40 is selected from a plurality of tendon clamp members of different sizes, the appropriate size being chosen so that the arcuate clamping element 60 of the tendon clamp member 40 fits closely around the perimeter of the patella 50 while resting only upon soft tissue, and not on the bone of the patella 50, as illustrated. Thus, once the patella clamp 20 is applied, the tendon clamp member 40 is moved toward the reference platform 30 until the soft tissue adjacent the patella 50 is engaged and patella 50 is extruded through the clamping element 60 of the tendon clamp member 40, as shown, and the quadriceps tendon and patellar ligament are taut. At that point, the patella clamp 20 is secured in place by locking the lower handle 26 against movement away from the upper handle 24, as by anchoring a lock 62 on a toothed lock rod 64 which is mounted to the upper handle 24 at 66 and which passes through the lower handle 26 at 68. A lock button 70 is selectively actuated to release the lock 62 for movement along the lock rod 64 and to lock the lock 62 in the selected location along the lock rod 64 which locks the lower handle 26 in place.

Figures 3, 4:
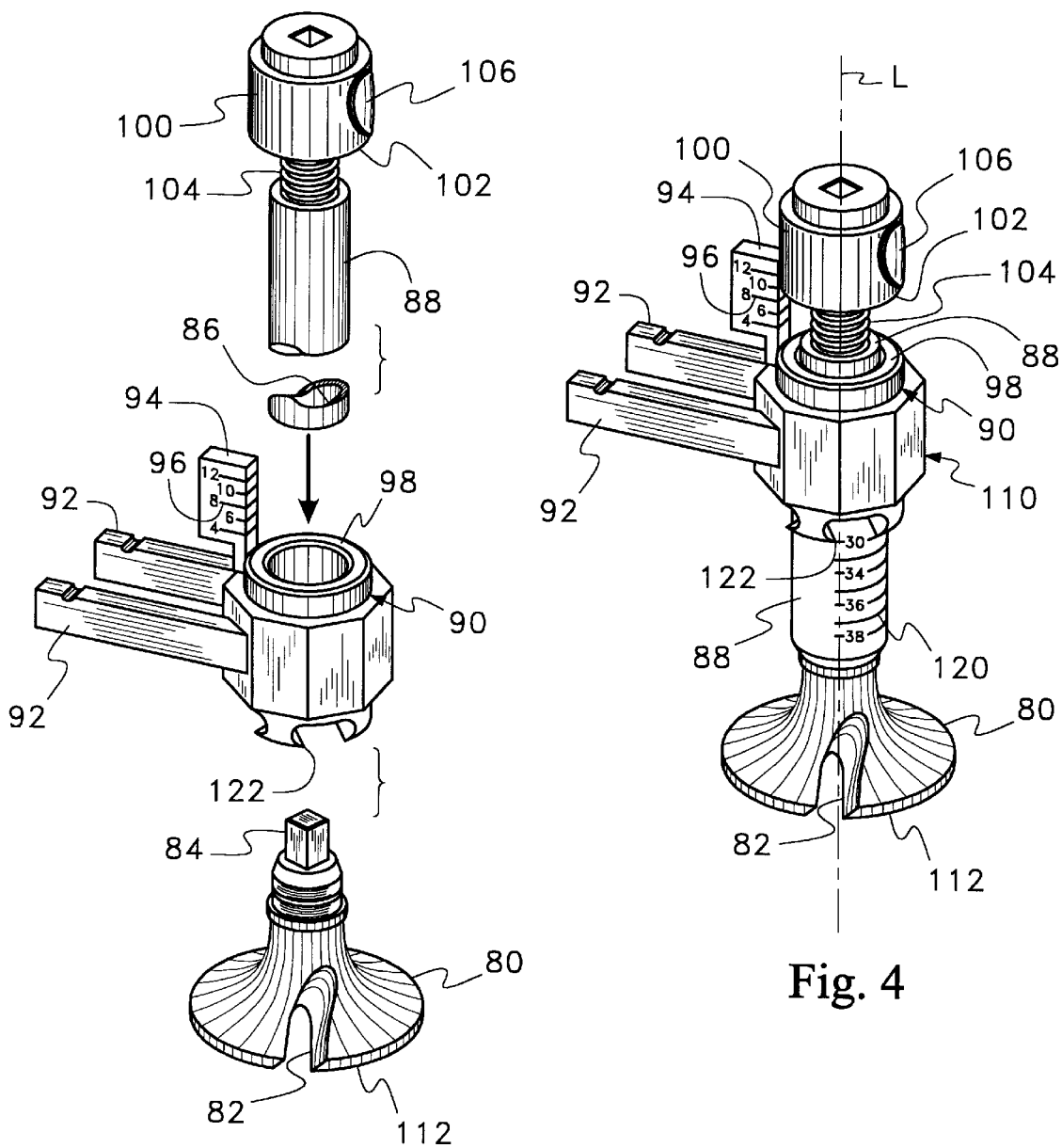
FIG. 3 is an exploded perspective view of another portion of the apparatus.
FIG. 4 is a pictorial perspective view of the portions of the apparatus shown in FIG. 3, with the component parts assembled for use.

Turning now to FIGS. 3 and 4, a bone-cutting tool is to be employed in the resection of the patella 50, and is shown in the form of a reamer 80 having a rotary cutter 82 and a drive pin 84 for rotating the cutter 82. The drive pin 84 is received within a tool holder shown in the form of a complementary drive socket 86 in the lower end of a reamer shaft 88 which is jounaled for rotation in a bushing member 90, about a longitudinal axis L of the bushing member 90, and which is free to move linearly within the bushing member 90 in directions along the longitudinal axis L. A pair of laterally extending posts 92 are carried by the bushing member 90, and an indicator in the form of a depth gauge 94 on the bushing member 90 includes a visible scale 96, for purposes to be described below. A first reference surface 98 extends laterally along the upper end of the bushing member 90. A stop member in the form of stop collar 100 includes a second reference surface 102 juxtaposed with and confronting the first reference surface 98, in opposition to the first reference surface 98, and is engaged with a toothed extension 104 at the upper end of the reamer shaft 88. The stop collar 100 is coupled to the toothed extension 104 by a coupler which includes an actuator button 106 selectively operated to release the stop collar 100 for movement longitudinally along the toothed extension 104 and to lock the stop collar 100 at a selected location along the toothed extension 104, for purposes to be described hereinafter.

Figure 5:
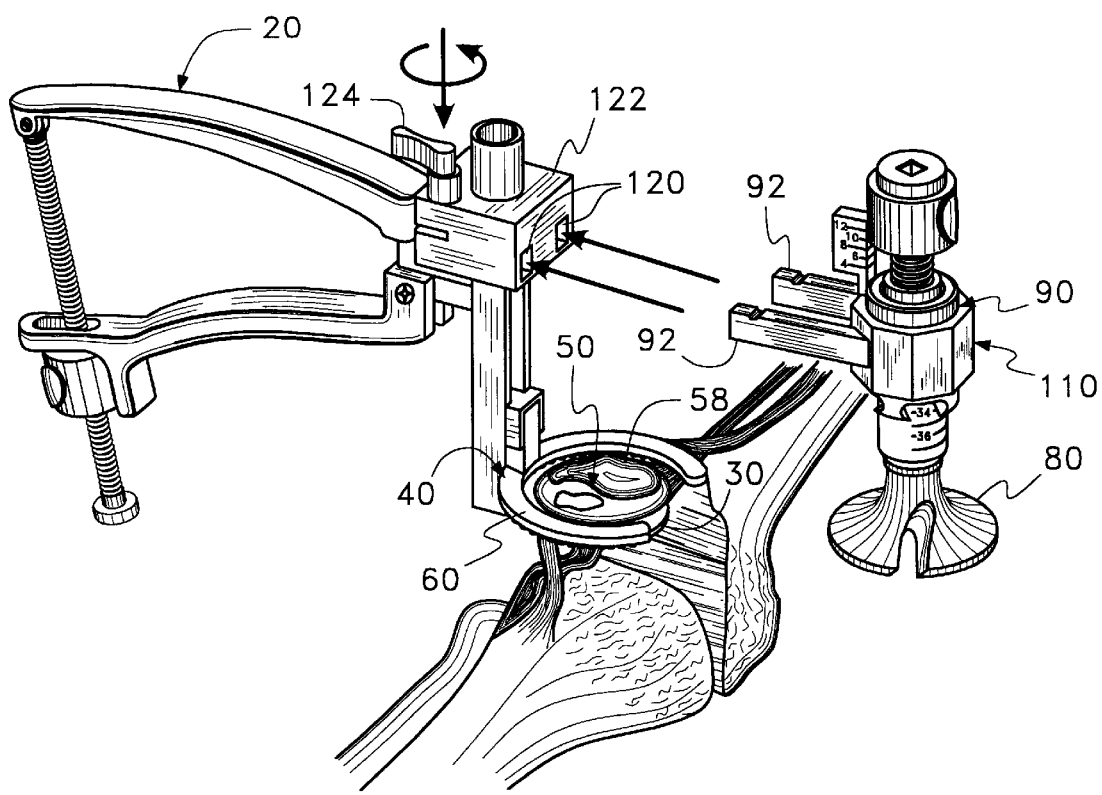
FIG. 5 is an exploded perspective view showing the assembly of the component parts of FIG. 4 with the portion shown in FIG. 2.
Figure 6:
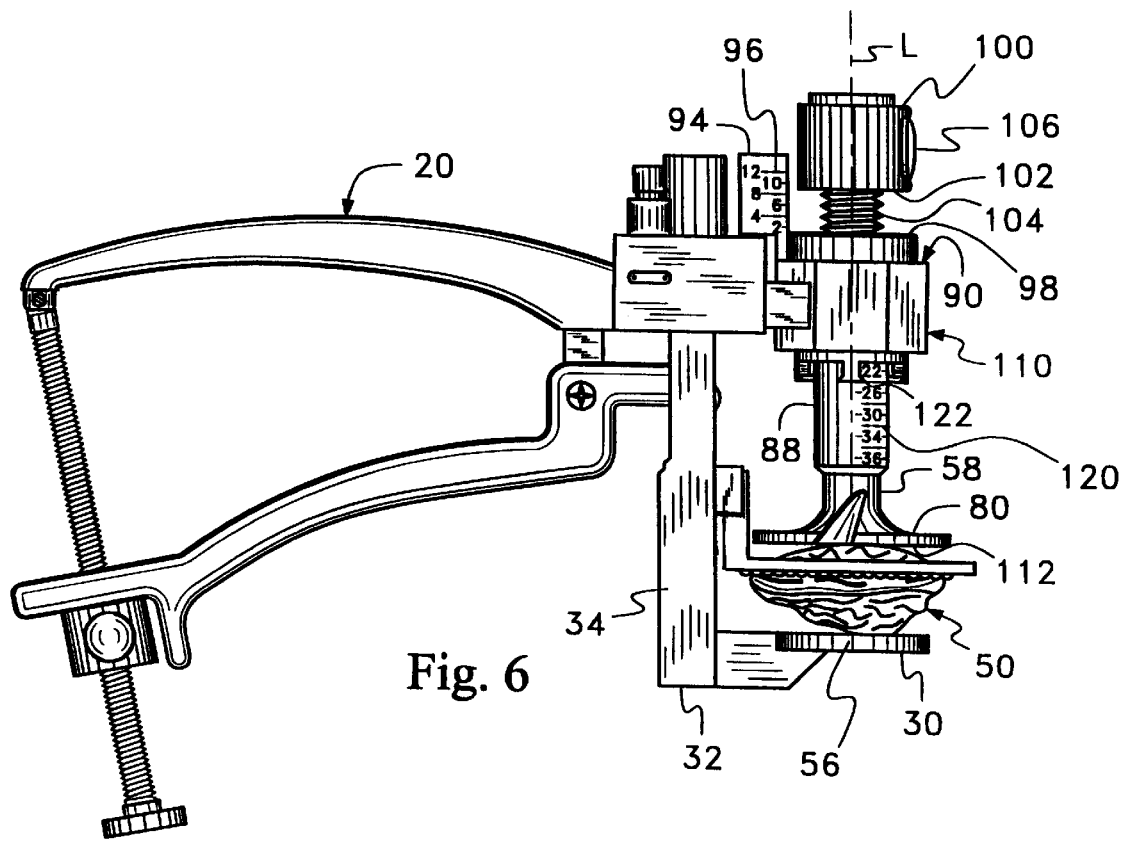
FIG. 6 is an elevational view showing the assembled apparatus in place prior to resection of the patella.
Figure 7:
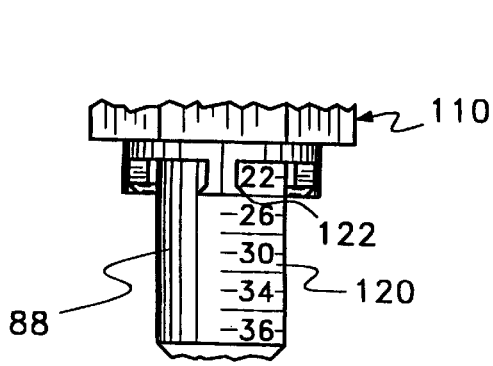
FIG. 7 is an enlarged fragmentary view of a portion of FIG. 6.

The assembled reamer 80, reamer shaft 88 and bushing member 90 together comprise a cutting assembly 110 which is then affixed to the patella clamp 20, as illustrated in FIG. 5. Posts 92 are inserted into complementary recesses 120 in a receptacle block 122 integral with the frame 22 of the patella clamp 20 to locate the bushing member 90 accurately in position in the patella clamp 20 relative to the platform reference surface 36 of the patella clamp 20, with the axis L intersecting the reference platform surface 36 at the preparation position. Then, a locking arm 124 is simultaneously depressed and rotated, as shown, to secure the cutting assembly 110 in the patella clamp 20. In the preferred arrangement, the bushing member 90 is oriented so that axis L is normal to the reference platform surface 36. Once the cutting assembly 110 is secured in the patella clamp 20, as illustrated in FIG. 6, the reamer 80 is allowed to drop downwardly, with the reamer shaft 88, until basal surface 112 of the reamer 80 rests upon the posterior surface 58 of the patella 50, as shown. At this point in the procedure, the surgeon is able to determine, with precision, the thickness of the patella 50 merely by observing an indicator in the form of a visible scale 120 on the reamer shaft 88 and a pointer 122 on the bushing member 90. Thus, as best seen in FIG. 7, as well as in FIG. 6, pointer 122 is located accurately relative to the platform reference surface 36 and scale 120 is calibrated in terms of distance between the basal surface 112 of the reamer 80 and the reference platform surface 36 upon which the anterior surface 56 of the patella 50 rests. In this manner, the surgeon is provided with a quick and accurate direct interoperative measurement which the surgeon will use to determine the amount of bone to be removed during subsequent resection of the patella 50, without the necessity for introducing supplementary instruments or interruption of the procedure.

Figure 8:
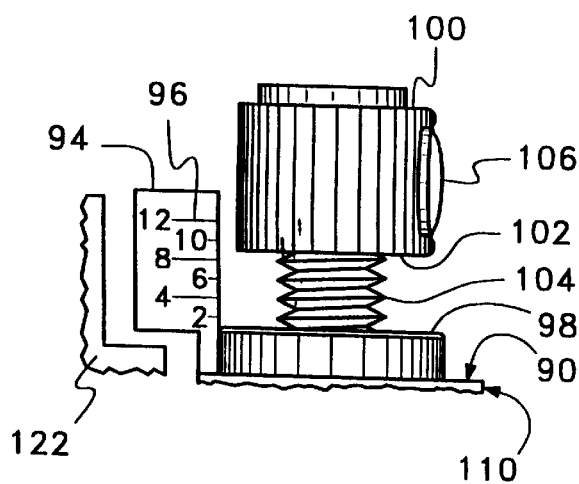
FIG. 8 is an enlarged fragmentary view of another portion of FIG. 6.

Once the surgeon determines the amount of bone to be removed during resection, the depth of resection is selected readily, again interoperatively, directly and without the necessity for supplemental instruments or other apparatus. Referring now to FIG. 8, as well as to FIG. 6, the longitudinal distance between the first reference surface 98 and the second reference surface 102 determines the extent of longitudinal travel of the reamer 80 as the reamer 80 resects the bone of the patella 50. Thus, by setting the position of the stop collar 100 on the toothed extension 104, the depth of resection is determined. Accordingly, scale 96 of depth gauge 94 is calibrated in terms of resection depth and the surgeon merely depresses actuator button 106 to release the stop collar 100 for movement along the toothed extension 104, locates the second reference surface 102 at the desired indicia mark along the scale 96, and then releases the actuator button 106 to lock the stop collar 100 in place, setting the longitudinal distance between the first and second reference surfaces 98 and 102 precisely to the desired depth of resection, all interoperatively, directly and without the necessity for additional instruments or other apparatus. The toothed configuration of extension 104 assures that the stop collar 100 is moved in precisely determined fixed longitudinal increments related to prescribed increments in the depth of resection. Typically, the increments are provided with a magnitude of one millimeter.

Figure 9:
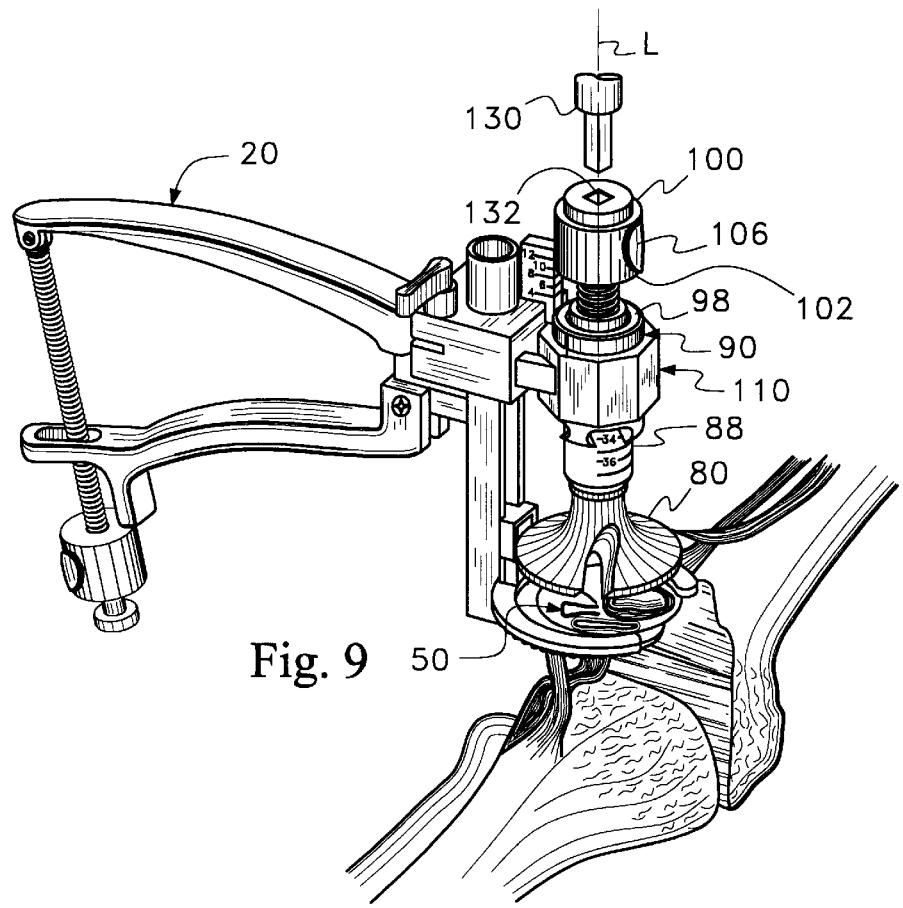
FIG. 9 is a pictorial perspective view of the apparatus just prior to resection of the patella.

As seen in FIG. 9, once the depth of resection is set, a powered shaft 130 is coupled with a power drive socket 132 located in the upper end of the reamer shaft 88, and the reamer 80 simultaneously is rotated about axis L and translated downwardly along axis L to execute the resection. Upon engagement of the second reference surface 102 with the first reference surface 98, resection is complete, with the depth of resection accurately determined in accordance with the setting of the stop collar 100.

Figure 10:
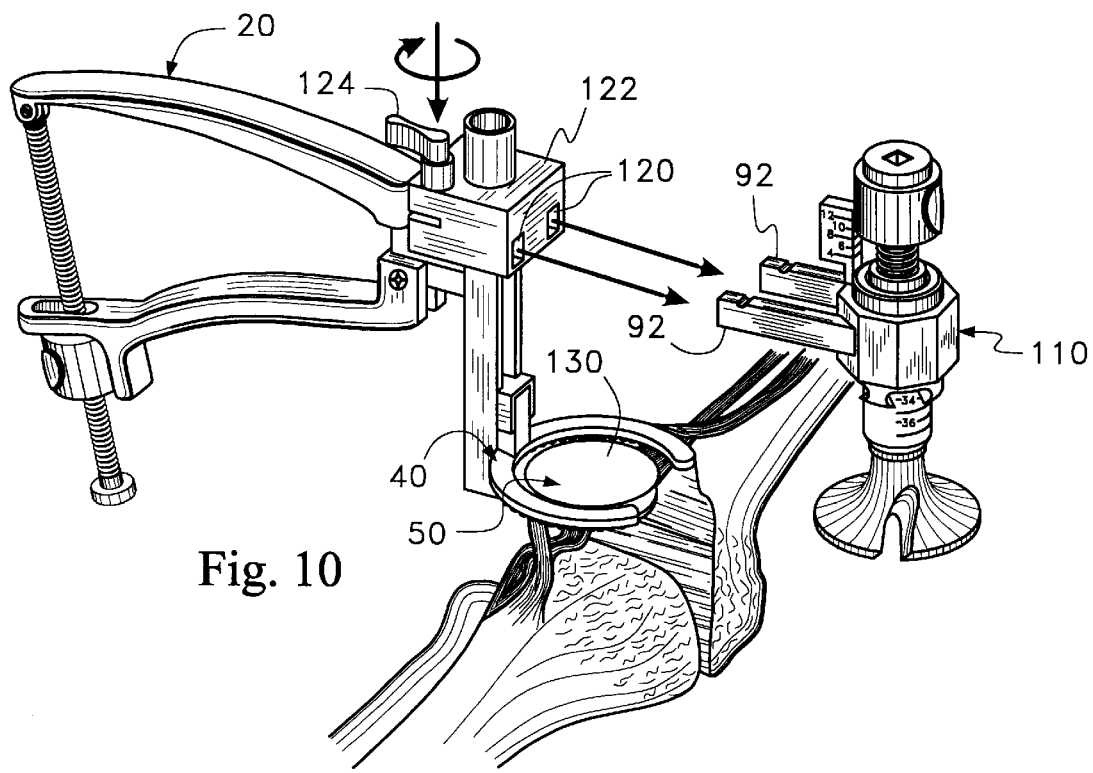
FIG. 10 is a pictorial perspective view, partially exploded, showing the apparatus just subsequent to resection of the patella.

The thickness of the resected patella 50 then may be read directly from the scale 102 on the reamer shaft 88. Should the surgeon determine that further resection is required, the stop collar 100 merely is reset to the desired further amount of resection and the reamer 80 then is advanced through the corresponding further amount of linear travel. Once resection is complete, the cutting assembly 110 is released and removed from the patella clamp 20 by reversing the previous procedure; that is, the locking arm 124 is simultaneously depressed and rotated to release the connection between the posts 92 and the receptacle block 122 and enable removal of the cutting assembly 110, as illustrated in FIG. 10, thereby exposing the newly created resected surface 130 of the resected patella 50. Resected surface 130 is essentially planar and normal to axis L.

Figure 11:
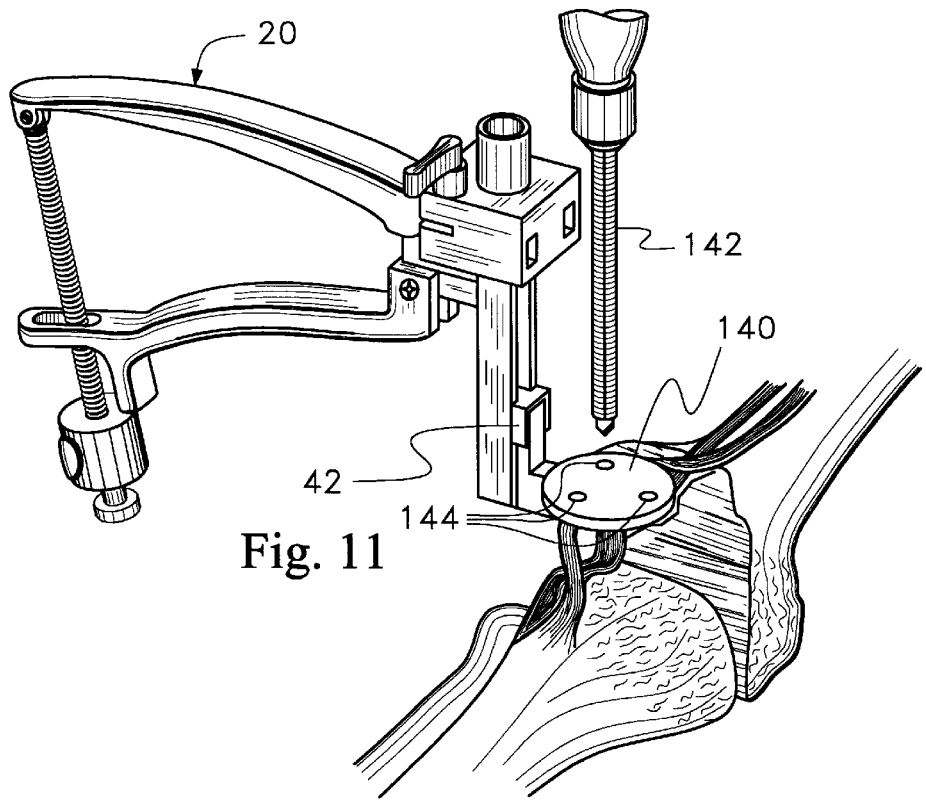
FIG. 11 is a pictorial perspective view showing a subsequent step in the preparation of the resected patella.

The tendon clamp member 40 then is removed from the patella clamp 20 and a drill template 140 is inserted into carrier 42 for juxtaposition with the resected surface 130 of the resected patella 50. With the patella clamp 20 secured in place so that the drill template 140 is located in position against resected surface 130, as illustrated in FIG. 11, a drill 142 is advanced through the apertures 144 in the drill template 140 for appropriate location of holes 148 (see FIG. 12) for corresponding lugs of a patellar prosthesis, such as patellar prosthesis 150 shown in FIG. 12. After removal of the patella clamp 20, and appropriate trial assessments, patellar prosthesis 150 is located against surface 130 of the resected patella 50, and is affixed to the patella 50, with the lugs 152 of the patellar prosthesis 150 entering the drilled holes 148.

Figure 12:
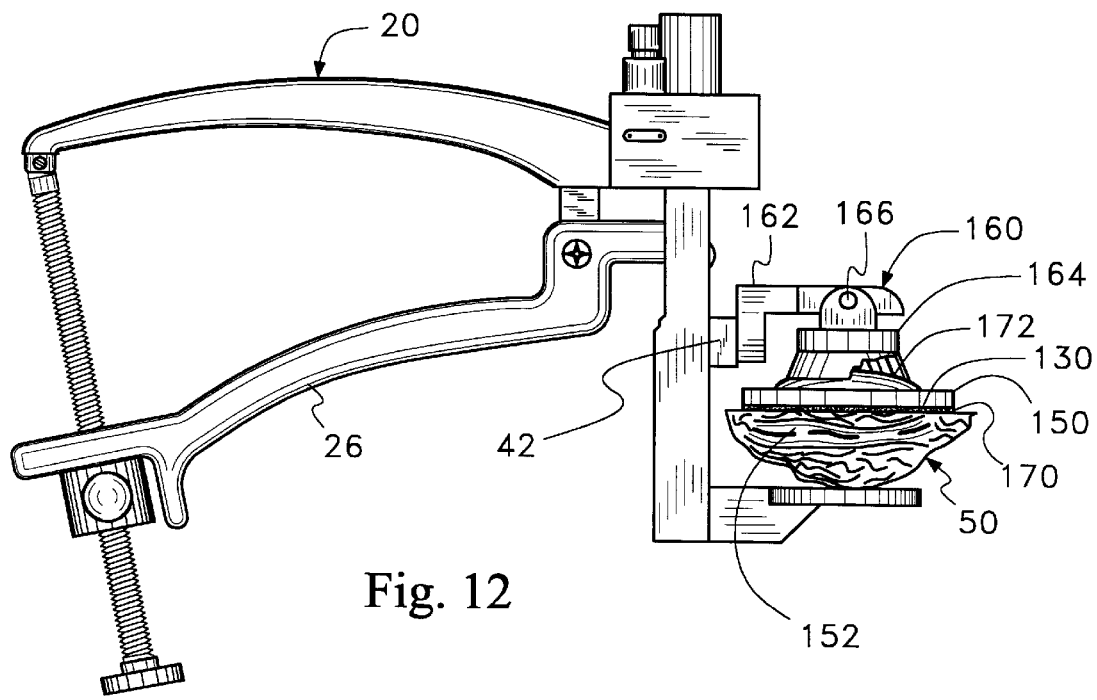
FIG. 12 is an elevational view showing the affixation of a patellar prosthesis to a patella in accordance with the present invention.

Affixation of the patellar prosthesis 150 to the resected patella 50 is assisted by inserting a retaining member in the form of an affixation adaptor 160 into the carrier 42 of the patella clamp 20 and applying the patella clamp 20 to the everted and resected patella 50, as illustrated in FIG. 12. Affixation adaptor 160 includes an arm 162 which is received in the carrier 42 for movement with the carrier 42, in response to movement of the lower handle 26 of the patella clamp 20, the arm 162 itself carrying a compression member 164 mounted upon the arm 162 at a pivot 166. Upon applying the patellar prosthesis 150 to the resected patella 50, with a layer of cement 170 interposed between the patellar prosthesis 150 and the resected surface 130 of the patella 50, the lower handle 26 is actuated to engage the compression member 164 with the patellar prosthesis 50, as shown, and to establish an affixation pressure between the patellar prosthesis 150 and the resected surface 130 of patella 50. The pivot 166 assists in appropriate alignment of the patellar prosthesis 150 while assuring that compression forces exerted by the compression member 164 are perpendicular to the interface between the patellar prosthesis 150 and the resected surface 130. In this manner, voids are avoided in the cement mantle during curing of the layer of cement 170. In the preferred construction, compression member 164 includes a somewhat cup-shaped concave engagement surface 172, and is constructed of a synthetic polymeric material.

Figure 13:
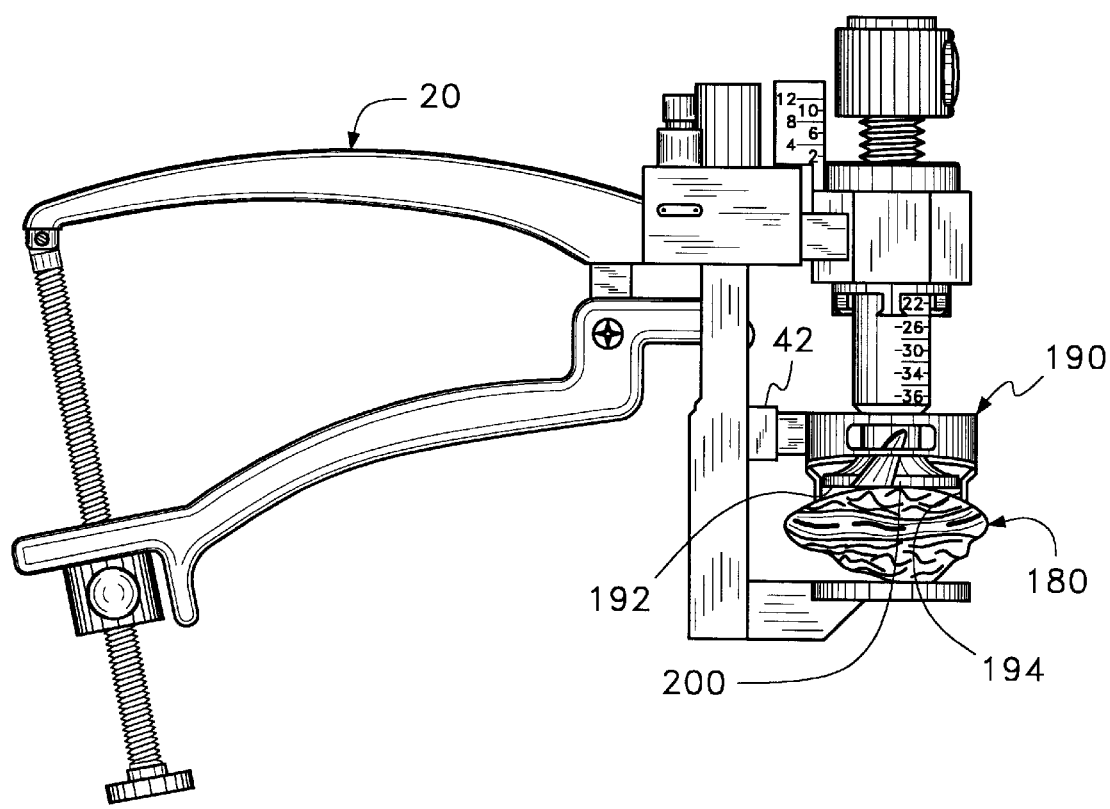
FIG. 13 is an elevational view of an alternate embodiment of the apparatus of the present invention, in place for the preparation of a patella.

In the alternate embodiment illustrated in FIG. 13, patella clamp 20 has been modified for recessed preparation of a patella 180. Thus, the retaining member is in the form of an annular reamer guide 190 placed within the carrier 42 and having a clamping rim 192 for retaining the patella 180 in the preparation position, and an internal passage 194 for guiding a reamer 200 which is to cut a recessed resection surface (not shown) into the patella 180 while the patella 180 is retained in the preparation position. All of the remaining component parts of patella clamp 20 are the same as described above, providing all of the same functions and advantages as set forth above.

It will be seen that the present invention attains all of the objects and advantages summarized above, namely: Enables increased ease and accuracy in effecting removal of predetermined amounts of natural bone for resection of the posterior patella in preparing the patella for reception of a patellar prosthesis; allows interoperative selection of the depth of resection with increased ease and accuracy, and without the necessity for interchanging component parts of the apparatus; permits immediate and accurate measurement of patella bone thickness prior to resection and then subsequent to resection, interoperatively, without requiring supplemental apparatus or component parts; facilitates the overall procedure for implanting a patellar prosthesis, thereby reducing operating time and concomitant trauma to the patient, while promoting greater precision in effecting the implant; provides a surgeon with greater versatility and a wider range of options during the implant procedure, with instruments of reduced complexity and increased ease of use; makes available apparatus of simplified and rugged construction, capable of reliable use with repeated accuracy over an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. Apparatus for the preparation of a patella to receive a patellar prosthesis on a resected surface located at a selected depth of resection, the patella having an anterior surface, a posterior surface and a bone thickness between the anterior surface and the posterior surface, the preparation including resection of the bone of the patella to the selected depth of resection, the apparatus comprising:

a frame;

a reference platform on the frame for supporting the patella in a preparation position, the reference platform including a reference platform surface extending laterally along the reference platform such that the anterior surface of the patella is located against the reference platform surface when the patella is in the preparation position;

a retaining member for mounting upon the frame in juxtaposition with the reference platform to hold the patella in the preparation position;

a bushing member for mounting upon the frame in juxtaposition with the reference platform, the bushing member including a longitudinal axis for intersecting the reference platform at the preparation position;

a tool holder for carrying a bone-cutting tool, the tool holder being receivable within the bushing member for linear movement along the longitudinal axis toward and away from the reference platform, and for rotational movement about the longitudinal axis, to locate and move the bone-cutting tool in juxtaposition with the reference platform;

a first indicator for direct interoperative indication of the longitudinal distance between the bone-cutting tool and the reference platform surface and, consequently, the bone thickness of the patella when the patella is in the preparation position and the bone-cutting tool is placed against the patella;

a first reference surface on the bushing member and extending laterally along the bushing member;

a stop member mounted on the tool holder for selective movement longitudinally along the tool holder interoperatively, the stop member having a second reference surface for juxtaposition in opposition to the first reference surface and including a coupler for interoperative coupling of the stop member with the tool holder at a selected location along the longitudinal axis, at which selected location the longitudinal spacing between the first reference surface and the second reference surface determines a desired depth of resection of the bone of the patella; and a second indicator for direct interoperative indication of the selected location of the stop member and, consequently, the selected depth of resection.

2. The invention of claim 1 wherein the stop member is mounted for movement along the tool holder in fixed longitudinal increments related to prescribed increments in the depth of resection.

3. The invention of claim 1 wherein the first indicator includes a scale on the tool holder for interoperative visibility, the scale being calibrated to indicate longitudinal distance between the bone-cutting tool and the reference platform surface for direct interoperative indication of the bone thickness of the patella when the patella is in the preparation position and the bone-cutting tool is placed against the patella.

4. The invention of claim 1 wherein the second indicator includes a scale located on the bushing member for interoperative visibility to enable direct viewing and selective setting of the desired depth of resection during preparation of the patella.

5. The invention of claim 4 wherein the stop member is mounted for movement along the tool holder in fixed longitudinal increments related to prescribed increments in the depth of resection.

6. The invention of claim 1 wherein the longitudinal axis is normal to the reference platform surface.

7. The invention of claim 1 wherein the retaining member is a tendon clamp member for engaging soft tissue adjacent the patella when the patella is in the preparation position.

8. The invention of claim 1 wherein the retaining member is a bone-cutting tool guide for engaging and retaining the patella in place in the preparation position and guiding the cutting tool into the posterior surface of the patella.

9. The invention of claim 1 wherein the retaining member is an affixation adaptor for engaging the patellar prosthesis when the patellar prosthesis is placed upon the resected surface and establishing an affixation pressure between the patellar prosthesis and the resected surface of the patella.

10. A method for the implant of a patellar prosthesis on a resected surface of a natural patella, the patella having an anterior surface, a posterior surface and a bone thickness between the anterior surface and the posterior surface, the method including resection of the bone of the patella to locate the resected surface at a selected depth of resection, the method comprising the steps of:

supporting the patella in a preparation position on a reference platform surface extending laterally along a reference platform such that the anterior surface of the patella is located against the reference platform surface when the patella is in the preparation position;

holding the patella in the preparation position;

juxtaposing a bushing member with the reference platform, the bushing member including a longitudinal axis for intersecting the reference platform at the preparation position;

placing a tool holder within the bushing member for carrying a bone-cutting tool for linear movement along the longitudinal axis toward and away from the reference platform, and for rotational movement about the longitudinal axis, to enable location and movement of the bone-cutting tool in juxtaposition with the reference platform;

providing a first indicator on the tool holder for direct and interoperative visual indication of the longitudinal distance between the bone-cutting tool and the reference platform surface and, consequently, the bone thickness of the patella when the patella is in the preparation position;

placing the bone-cutting tool against the posterior surface of the patella held in the preparation position to determine the bone thickness of the patella directly and interoperatively, prior to resection;

providing a first reference surface on the bushing member and extending laterally along the bushing member;

selectively moving a stop member longitudinally along the tool holder interoperatively, the stop member having a second reference surface for juxtaposition in opposition to the first reference surface, and interoperatively coupling the stop member with the tool holder at a selected location along the longitudinal axis, at which selected location the longitudinal spacing between the first reference surface and the second reference surface determines a desired depth of resection of the bone of the patella;

providing a second indicator on the bushing member for direct and interoperative visual indication of the selected location of the stop member and, consequently, direct determination of the selected depth of resection;

advancing the bone-cutting tool longitudinally along the longitudinal axis until the second reference surface engages the first reference surface; and viewing the first indicator for a direct and interoperative indication of the bone thickness of the patella subsequent to resection.

11. The invention of claim 10 including affixing the patellar prosthesis to the resected surface of the patella.

* * * * *